United States Patent [19]

Daley et al.

[11] Patent Number: 5,342,612
[45] Date of Patent: Aug. 30, 1994

[54] COMPOSITIONS FOR THE TREATMENT OF MAMMALIAN DISEASES

[75] Inventors: Michael J. Daley, Yardley, Pa.; William D. Steber, Ledgewood; Gary J. Furda, Trenton, both of N.J.; Paul A. Johnston, Langhorne; Elizabeth R. Oldham, Newtown, both of Pa.

[73] Assignee: American Cyanamid Company, Wayne, N.J.

[21] Appl. No.: 812,894

[22] Filed: Dec. 20, 1991

[51] Int. Cl.$^5$ .............................. A61K 45/05
[52] U.S. Cl. .................... 424/85.1; 514/2; 514/12; 514/24
[58] Field of Search ............... 514/2, 12, 24; 424/85.1, 85.2, 85.4, 94.3

[56] References Cited

U.S. PATENT DOCUMENTS

| | | | |
|---|---|---|---|
| 3,278,378 | 10/1966 | Schindler et al. | 424/115 |
| 3,398,056 | 8/1968 | Zygmunt et al. | 435/71.3 |
| 3,594,284 | 7/1971 | Zygmunt et al. | 435/220 |
| 4,156,719 | 5/1979 | Sezaki et al. | 424/118 |
| 4,457,916 | 7/1984 | Hayashi et al. | 530/351 |
| 4,469,228 | 9/1984 | Zupon et al. | 206/568 |
| 4,478,822 | 10/1984 | Haslam et al. | 424/78 |
| 4,606,918 | 8/1986 | Allison et al. | 424/88 |
| 4,650,674 | 3/1987 | Aggarwal et al. | 424/85.5 |
| 4,803,072 | 2/1989 | Dalton et al. | 514/2 |
| 4,857,506 | 8/1989 | Tyle | 514/12 |
| 4,944,941 | 7/1990 | Ammann | 424/85.5 |
| 4,980,163 | 12/1990 | Blackburn et al. | 514/2 X |
| 5,071,644 | 12/1991 | Viegas et al. | 514/772.7 |
| 5,124,145 | 6/1992 | Sordillo et al. | 424/85.5 |
| 5,135,910 | 8/1992 | Blackburn et al. | 514/2 |
| 5,183,746 | 2/1993 | Shaked et al. | 530/351 |

FOREIGN PATENT DOCUMENTS

88/6446  8/1989  South Africa .

OTHER PUBLICATIONS

"Information on on Applications of Pluronics" by Wyandotte Chemicals Corporation, Mar. 1, 1952.

Recsei et al., Cloning, sequence and expression of the lysostaphin gene for *Staphylococcus simulans,* Proc. Natl. Acad. Sci. USA, vol. 84, pp. 1127–1131 (Mar. 1987).

Oldham et al., Lysostaphin: Use of a Recombinant Bactericidal Enzyme as a Mastitis Therapeutic, J. Dairy Sci., vol. 74, pp. 4175–4182 (1991).

Daley et al., Quantitative and qualitative properties of host polymorphonuclear cells during experimentally induced *Staphylococcus aureus* mastitis in cows, Am. J. Vet. Res., vol. 52, No. 3, pp. 474–479 (mar. 1991).

Primary Examiner—Michael G. Wityshyn
Assistant Examiner—C. Sayala
Attorney, Agent, or Firm—Michael P. Morris

[57] ABSTRACT

A therapeutic composition which contains a potentiating or safening amount of an aqueous surfactant in combination with a bactericidal agent and/or a biological response modifier is described herein. The disclosure further describes an improved method for treating mastitis by administering the composition to an afflicted mammal. Additionally, the disclosure describes a method for screening suitable formulations for treating infectious diseases.

1 Claim, No Drawings

COMPOSITIONS FOR THE TREATMENT OF MAMMALIAN DISEASES

BACKGROUND OF THE INVENTION

1. Field of the Invention

The present invention relates to new compositions in the treatment of mammalian diseases containing an aqueous surfactant in combination with a bactericidal agent or a biological response modifier to effectively enhance the biological activity and/or decrease the undesirable side effects thereof.

2. Description of the Related Art

Infectious diseases are a leading cause of hospitalization and morbidity in human and veterinary medicine. Improved methods of prevention and therapy remain a major unfilled need in medicine. Despite significant progress in infectious disease control due to widespread adoption of aseptic practices and antibiotic treatment, many infectious diseases remain refractory to treatment. In veterinary medicine, for example, clinical bovine mastitis is of serious economic importance and causes annual losses of an estimated $2 billion to dairy farmers in the United States alone, primarily due to discarded milk with antibiotic residues. One of the foremost etiological agents contributing to this loss is *Staphylococcus aureus*. Intramammary infections caused by *S. aureus* are usually chronic and subclinical in nature. The current treatment for *S. aureus* mastitis is antibiotic therapy. The conventional therapy is nevertheless considered undesirable because of its moderate to low efficacy in producing only a 25% to 50% cure rate and because of the typical three to four day milk discard due to antibiotic residues. The ineffectiveness of current antibiotic therapy has been attributed to some antibiotic resistant strains of *S. aureus* and to the sequestration of *S. aureus* within the host's cell. For this reason, bovine mastitis provides a valuable in vivo model to study infectious diseases of mammals.

Mucolytic peptides, such as lysostaphin, have been suggested to be efficacious in the treatment of *S. aureus* infections of humans (Schaffner et al., Yale J. Biol. & Med., 39:230 (1967) and bovine mastitis caused by *S. aureus* (Sears et al., J. Dairy Science, 71 (Suppl. 1): 244(1988)). Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393–400 (1965)). U.S. Pat. No. 3,278,378 describes fermentation methods for producing lysostaphin from culture media of *S. staphylolyticus*, later renamed *S. simulans*. Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127–1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62–68 (1968)). However, in vivo studies by Oldham, et al., J. Dairy Science, 74:4413 (1991), have demonstrated that the therapeutic efficacy of lysostaphin is not equivalent to the commercially available product CEFA-LAK® (cephapirin sodium, available from Bristol-Meyers, Evansville, Ind.).

Polymorphonuclear neutrophils (PMNs) also play a critical role in the pathophysiology of most bacterial infections. For example, it has been found that greater than 90% of the cells in an infected gland are PMNs (Daley et al., American Journal of Veterinary Research, 52 (3): 474–479 (1991)). PMNs demonstrate 10,000 fold variation in the efficiency of intracellular killing of *S. aureus* during somatic cell count cycling. PMNs from a gland infected with *S. aureus* are both quantitatively (total somatic cell count) and qualitatively (intracellular killing and phagocytic ability) different during the course of a cycling infection. Both the quantity and quality of phagocytic cells play a central role in the defense of the host against infections. It is seen that PMN activity (especially phagocytosis and intracellular killing) can be specifically manipulated using recombinant bovine cytokines and other bioresponse modifiers in the bovine mammary gland to elicit mastitis cures.

A number of cytokines stimulate the growth and differentiation of hematopoietic and other somatic cells. For example, a cytokine such as GM-CSF is able to increase the development of granulocytes and macrophages. Lymphokines such as IL-2 are found to be secreted by T cells when stimulated by antigenic substances and IL-2 receptors have been described to be expressed by T cells, B cells, macrophages and specialized epithelium. Methods for preparing cytokines are well described in the literature (see, for example, Cerretti et al., Cloning sequence and expression of bovine interleukin-2, P.N.A.S., 83:3223–3227 (1986); Maliszewski et al., Cloning, sequence and expression of bovine interleukin $1_a$ and interleukin $1_b$ complementary DNAs, Molecular Immunology, 25:429–435 (1988); Maliszewski et al., Bovine GM-CSF: Molecular cloning and biological activity of the recombinant protein, Molecular Immunol., 25: 843–50 (1988); March et. al., Cloning, sequence and expression of two distinct human interleukin-1 complementary DNAs, Nature, 315:641–648 (1985)). Many cytokine genes have been cloned, expressed and characterized making possible the employment of recombinantly derived proteins in the therapy of a variety of hematopoietic and immune diseases (Cantrell et al., Proc. Natl. Acad. Sci. USA, 82:6250–6254 (1985)). Many of these immunomodulators, however, cause certain undesirable side effects which severely limit their practical usefulness (Winkelhake et al., Human recombinant interleukin-2 as an experimental therapeutic, Pharmacological Rev., 42:1 (1990); Taguchi, Clinical effects of interferon on malignancies, Japan J. Cancer Chemo., 11:194 (1984); Dinarello et al., Multiple biological activities of human recombinant interleukin-1, J. Clin. Invest., 77:1734 (1986)).

Ideally, the composition useful in infectious disease therapy should be optimized for efficacy, have minimal residues and have minimal toxic effects. Considering the level of efficacy of the currently available commercial preparations for some infectious diseases, new therapeutics which would have improved biological potency with little or no side effects are highly desirable.

OBJECTS OF THE INVENTION

It is therefore an important object of the present invention to provide highly unique compositions for the treatment of infectious diseases which possess significantly improved bactericidal activity.

Another object is to provide safened compositions for use in infectious diseases which decrease the undesirable side effects of the active ingredient.

A further object is to provide an efficacious mastitis therapeutic agent with no or minimal milk discard.

Another further object is to provide an improved method for treating bovine mastitis which utilizes an efficacious and/or safened therapeutic agent.

Yet another object is to provide a new method for identifying safe and efficacious formulations using in vitro techniques and the bovine mammary gland.

Further purposes and objects of the present invention will appear as the specification proceeds.

SUMMARY OF THE INVENTION

The foregoing objects are accomplished by providing a composition comprising an aqueous surfactant in combination with a bactericidal agent and/or a biological response modifier. The products of this invention are highly efficacious with minimal side effects. The present invention further embraces an improved method for treating infectious diseases in mammals which involves administering the aforesaid composition to a mammal to effect a cure and/or to decrease unwanted side effects from therapy. The background of the invention and its departure from the art will be further described hereinbelow.

DETAILED DESCRIPTION OF THE INVENTION

In accordance with the present invention, there is provided a novel composition as an effective therapeutic agent in mammalian diseases which employs an aqueous surfactant in combination with a bactericidal agent or a biological response modifier wherein said surfactant beneficially enhances the biological activity and/or decreases the undesirable side effects of the bactericidal agent or the biological response modifier.

Desirably, criteria for selecting the surfactant for formulation are: (1) nontoxic to mammalian cells, that is, for example, the vehicle is not substantially toxic to mammalian tissue culture cells and can be safely administered in vivo into the mammary gland (preferably GRAS, generally regarded as safe), (2) ability to increase the stability of the active ingredient, (3) ability to maintain the immunopotentiating effects while minimizing any systemic side effects such as toxicity and (4) ability to significantly potentiate the bacteriostatic and/or bactericidal activity against S. aureus or other infectious agents by the active ingredient.

Following the aforesaid criteria, examples of aqueous surfactants useful in this invention would include, but are not limited to, polyglycols such as polyoxypropylene-polyoxyethylene block copolymers; sterols such as soya sterol having 10–25 moles of ethylene oxide (GENEROL®, commercially available from Henkel Corp., Hoboken, N.J.); polyhydric alcohols such as glycerol; esters of glycerin such as triacetin (also known as glyceryl triacetate); n-dodecylglucosid; decanoyl-n-methylglucamid; dodecyl B-D-maltosid; octanoyl-n-methylglucamid and the like. A particularly preferred nonionic surfactant is a polyoxypropylene-polyoxyethylene block copolymer also known generically as poloxamer 407 NF. The aqueous surfactant is found in the composition in varying potentiating or safening amounts but may range from about 0.01% to about 15% by weight. Desirably, the surfactant is present in the composition in the amount of about 1% to about 7.5% by weight.

The bactericidal agent which would be useful in infectious diseases may be a bacteriolytic peptide such as an enzyme or bacteriostatic peptide, for example, lysostaphin, lysozyme, nisin, magainins and the like. This active ingredient is present in the composition in varying amounts but usually from about 0.01% to about 50% by weight of the total composition and desirably, from about 0.1% to about 7.5% by weight. As an alternative to the bacteriolytic enzymes, the aqueous surfactant may be formulated with antibiotics such as amoxicillin, ampicillin, cephapirin, cloxacillin, hetacillin, penicillin G, etc.

The other active ingredient which may be present in the composition of the present invention is a biological response modifier such as an immunomodulator (e.g., the cytokines) or a polypeptide hormone. Examples include, but are not limited to, recombinant interleukin(s), colony stimulating factors, interferons, tumor necrosis factors, other cellular factors and the like. This ingredient is present in the composition in varying amounts but usually from about 0.001% to about 7.5% by weight of the total composition and desirably, from about 0.01% to about 1.0% by weight.

Typically, an inert, conventional carrier is included in the composition in varying amounts which, of course, will be dependent upon the amounts and the desired dosages selected for the other ingredients.

Optionally, the composition may also contain a secondary biological response modifier such as a chemotractant or a chemoactivator of phagocytic cells. The combined therapy of lysostaphin and a chemotractant in past in vitro studies demonstrate that milk PMNs activated by the chemotractant are most efficient in terms of their ability to phagocytize. In addition, in vivo efficacy trials show that certain biological response modifiers such as lipopolysaccharide are able to clear the mammary gland temporarily of S. aureus. When present, the secondary biological response response modifier is found in the composition in varying amounts but can range from about 0.001% to about 7.5% by weight. The secondary biological response modifiers include any compound which elicits an influx of neutrophils or appropriate cell type into the mammary gland, for example, lipopolysaccharide, zymosan, protein A, oyster glycogen, enterotoxin B, various components of infectious disease causing organisms, other similar factors derived from infectious agents and the like.

For an example, a preferred formulation may contain a polyoxypropylene-polyoxyethylene block copolymer in the amount of about 0.01% to about 15% and lysostaphin in the amount of about 1.0% to about 7.5%, on a weight basis. Another example of a formulation according to the present invention would comprise a polyoxypropylene-polyoxyethylene block copolymer in the amount of about 0.01% to about 15% and recombinant bovine interleukin-2 in the amount of about 0.01% to about 50%, on a weight basis. A third example would be a formulation containing a polyoxypropylene-polyoxyethylene block copolymer in the amount of about 0.01% to about 15%, lysostaphin in the amount of about 0.1% to about 7.5% and recombinant bovine interleukin-2 in the amount of about 0.01% to about 50%, on a weight basis.

Advantageously and surprisingly, by using the active ingredient in combination with the aqueous surfactant, a therapeutic formulation is produced which is highly effective in acute and chronic infections in mammals, as exemplified by treating bovine mastitis. The formulations containing the active ingredients are typically administered parenterally, for example, by direct injection into the afflicted organ (i.e., intramammary), subcutaneously or intravenously. Alternatively, the formulations may be administered topically or orally in a wide range of therapeutic dosages. Lysostaphin, for example, is usually administered parenterally in multiple doses in the amounts of about 0.5 mg to about 500 mg, and preferably, about 100 mg. Recombinant bovine interleukin-2 is also typically administered parenterally in the amounts of about 0.1 mg to about 40 mg, and preferably, about 10 mg. Nevertheless, dosages that are either above or below the specified ranges can also be used, though generally less favorably.

As a specific example in the case of bovine mastitis, a formulated product using the surfactant with the bactericidal agent produces minimal changes in the quality of milk produced by the dairy cattle and probably would need little or no milk discard. Also beneficially, the surfactant significantly potentiates the therapeutic efficacy of the bactericidal agent and the biological response modifier. Equally advantageously, there is a substantial decrease in the clinical signs in animals which have been treated with cytokines formulated with an aqueous surfactant. Undesirable side effects such as fever, malaise and diarrhea have limited the practical use of the cytokines in bovine mastitis in the past. It has now been observed that recombinant bovine interleukin-2, a cytokine having particularly severe side effects, in a polyoxypropylenepolyoxyethylene block copolymer is substantially less detrimental to an animal than infusions of r-BoIL-2 in sterile phosphate buffered saline. Therefore, with an effective increase in phagocytic cells, superoxide production and phagocytosis by milk cells, the concomitant lessening of clinical signs is extremely beneficial to effective cytokine treatments.

While this application describes the use of the compositions in mastitis therapy, it is additionally contemplated that the compositions would be useful in any acute inflammatory disease which would benefit from immunomodulatory therapy. For example, the safening agent may find utility in cancer therapy or other related mammalian diseases.

In order to identify the nontoxic formulations for mammalian use, toxicity is employed as a method to eliminate direct bactericidal effects on the S. aureus, as well as potential toxic effects on the target animal. Compounds are formulated with r-lysostaphin at concentrations below toxic effects and compared to the bacteriostatic activity of r-lysostaphin in a saline formulation. Some compounds potentiate r-lysostaphin bacteriostatic activity by as much as 300–1000 fold. A checkered analysis to evaluate the relative contribution of each compound to this potentiation suggests that most of these compounds interact with the r-lysostaphin to increase its bioavailability or enzymatic activity. Formulations which demonstrate the best potentiation are also evaluated as an in vivo therapeutic.

In accordance with the present invention, an approach is taken where r-lysostaphin is formulated with chemicals that show in vitro bacteriostatic and/or bactericidal potentiation with minimal toxicity. These chemicals, subsequently referred to as "vehicles," are evaluated in vivo. Once r-lysostaphin's potentiation is targeted by the in vitro screens of vehicles, these vehicles are evaluated in vivo with the concept of developing a product that can supersede the efficacy of the commercial standard, CEFA-LAK®, with little or no necessity for milk discard. The preliminary in vitro screens find utility in predicting effective formulations of r-lysostaphin. The broader applications of these observations for other bacteriolytic enzymes as potential therapeutics are also possible by the methods of this invention. The approach to identifying the nontoxic formulations of the present invention is summarized below:

SUMMARY OF CRITERION FOR INCLUSION OF VEHICLE IN FURTHER EVALUATIONS

I. Nontoxicity
  A. *Staphylococcus aureus* in vitro (M.I.C.)
    1. further evaluation for potentiation performed at diluted concentrations with little or no toxicity
  B. Mammalian cells in vitro (viability at 6 hours +72 hours)
    1. Murine tumor cell lines
  C. Mammary gland irritation
    1. Induction of somatic cell count after intramammary infusion at 12, 24 and 48 hours
  D. Lack of clinical signs (edema, fever, diarrhea)
II. Compound Listed as Gras (generally regarded as safe)
  A. GRAS compounds showing suitable potentiation can probably be used in a therapeutic to be included in a consumed animal product (milk) or can be well tolerated during any therapeutic modality
III. In Vitro Effects on r-Lysostaphin
  A. Increased stability in milk
  B. Increased bacteriostatic/bactericidal activity IV. In Vivo Effects on r-Lysostaphin A. Increased residence time in the mammary gland V. In Vivo Efficacy Greater Than or Equal to CEFA-LAK® (Mastitis Antibiotic)

The above-noted series of in vitro and in vivo screening criteria can identify a number of chemical vehicles and classify them as possible candidates for further in vivo evaluation. These criteria include minimal in vitro and in vivo toxicity and maximal in vitro potentiation of the bacteriostatic and/or bactericidal activity of r-lysostaphin. In vivo trials with r-lysostaphin formulated with poloxamer 407 NF, for example, confirm the in vitro potentiation data and identify the poloxamer 407 NF as a compound which enhances the efficacy of r-lysostaphin by approximately two-fold. These experiments using r-lysostaphin may therefore be utilized as a model system in which to evaluate other compounds that may potentiate the bacteriolytic activity of a variety of enzymes, peptides and/or recombinant proteins that may have application as a mastitis therapeutic.

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

Toxicity of polymer 407 NF, Glycerol, Triacetin and Glyceryl Monocaprylate on Murine Cell Lines

Materials

Cell Lines: A20: B-cell tumor cell line 9C127: T-cell hybridoma cell line LB/62287: B-cell lymphoma cell line P388.D1: Macrophage tumor cell line Vehicles: 15% w/v Poloxamer 407 NF (PLURONIC® ACID F127; polyoxyethylene-polyoxypropylene derivative, BASF Corporation, Parsippany, N.J.) prepared in sterile phosphate buffered saline 50% w/v Glycerol (Sigma Chemical Co., St. Louis, Mo.) prepared in sterile phosphate buffered saline 10% w/v Triacetin (glyceryl triacetate, Sigma Chemical Co., St. Louis, Mo.) prepared in sterile phosphate buffered saline 10% w/v Glyceryl monocaprylate (IMWITOR® 308, Hüls American Inc., Piscataway, N.J.)

Control: 60.0 mL sterile phosphate buffered saline (sPBS)

Procedure

Cell lines ($1 \times 10^5$/well; >85% viability) are cultured in 24 well flat bottom plates in RPMI® medium (Gibco Laboratories, Grand Island, N.Y.) supplemented with 10% fetal calf serum, streptomycin (100 μg/mL) and penicillin (100 U/mL). Cultures are incubated (37° C., 10% $CO_2$) with the following concentrations of vehicles:

a) 1.5%, 0.15% or 0.015% PLURONIC® F127
b) 5.0%, 0.5% or 0.05% Glycerol
c) 1.0%, 0.1% or 0.01% Triacetin or IMWITOR®

After a 72 hour or 6 hour incubation period, cells are harvested and counted by the Coulter Counter (Northwell Drive, England). Cell viability is determined using a Coulter Channelyzer.

Discussion

The relative toxicity of the sample formulations to estimate the relative degree of toxicity for in vivo administration is carried out in vitro with the mammalian cell lines. Various concentrations of the vehicles are incubated for either 6 or 24 hours with the different mammalian cell lines. Immediate toxicity is evaluated at 6 hours by quantitating the number of dead cells in treated wells as compared to the untreated controls. Long term toxicity effects as well as effects which may inhibit cell growth are evaluated by measuring the relative degree of proliferation after an additional 48 hours incubation with $^3$H-thymidine. The toxicity data are summarized in Table I.

TABLE I

| | | TOXICITY OF FORMULATIONS ON MAMMALIAN CELL LINES | | | | | | | |
|---|---|---|---|---|---|---|---|---|---|
| | Concentration (%) | Realtive Toxicity at 6 Hours | | | | Relative Toxicity at 72 Hours | | | |
| Vehicle | | A20 | 9C127 | P388.D1 | LB | A20 | 9C127 | P388.D1 | LB |
| PLURONIC® F 127 | 1.5 | + | − | − | | +++ | ++++ | + | |
| PLURONIC® F 127 | 0.15 | + | − | ++ | | +++ | +++ | + | |
| PLURONIC® F 127 | 0.015 | − | − | ++ | | +++ | ++ | ++ | |
| Glycerol | 5.0 | ++ | ++++ | + | | +++ | ++++ | + | |
| Glycerol | 0.5 | + | ++ | +++ | | ++ | ++ | + | |
| Glycerol | 0.05 | − | ++ | +++ | | ++ | − | ++ | |
| IMWITOR® | 1.0 | ++ | | + | +++ | +++ | | +++ | ++++ |
| IMWITOR® | 0.1 | ++ | | + | +++ | ++++ | | +++ | ++++ |
| IMWITOR® | 0.01 | − | | + | ++ | − | | ++ | ++ |
| Triacetin | 1.0 | + | | | − | ++++ | | | ++++ |
| Triacetin | 0.1 | − | | | + | + | | | − |
| Triacetin | 0.01 | − | | | − | − | | | − |

[1]Toxicity is scored as (−) if no toxicity is seen as compared to controls. Toxicity is scored as (+), 75–90%; (++), 50–74%; (+++), 25–49%; (++++), 0–24% of the viability of the untreated controls. Consistent scoring of (++++) at all time points suggests significant toxicity.

EXAMPLE 2

Irritation of the Mammary Gland by Poloxamer 407 NF, Glycerol and Triacetin

Vehicles which demonstrate either no toxicity or limited toxicity based on the results from the methods in Example 1 or which can be diluted to eliminate toxic effects are then evaluated for in vivo irritation of the mammary gland.

Procedure

Multiparous Holstein-Fresian dairy cattle cultured negative for infection and with individual quarter somatic cell counts less than 200,000 cells/mL are used. The lactating dairy cows receive a ration consisting of corn silage, alfalfa hay and concentrate which is formulated to provide recommended amounts of minerals and vitamins for a lactating dairy cow. Water is provided ad libitum.

The somatic cell count (SCC) of twelve normal glands are determined prior to treatment. Three groups of four quarters each receive an intramammary infusion of 10 mL to 60 mL of the respective vehicles identified in Example 1, 15% w/v poloxamer 407 NF (PLURONIC® F127), 50% w/v glycerol, 10% w/v triacetin (glyceryl triacetate) and the sPBS as a control. In vivo degree of irritation is measured by infusing a quarter of a mammary gland with the vehicle and measuring the SCC at 12, 36 and 60 hours after infusion. The data are expressed as the stimulation index which is calculated as the average experimental SCC divided by the control SCC.

Discussion

All vehicles as selected by in vitro criteria are well tolerated by the animals. A small amount of irritation to some animals is noted upon infusion of the triacetin. The poloxamer 407 NF induces a moderate SCC elevation for up to 36 hours after infusion. Similar increases in SCC are not seen for either the 50% glycerol or 10% triacetin vehicles. However, all these changes are modest compared to influxes of somatic cells after infusion of endotoxin or other bacterial components (100–5000 fold). The results are summarized in Table II.

TABLE II

| IRRITATION OF THE MAMMARY GLAND BY VEHICLES (STIMULATION INDEX) | | | |
|---|---|---|---|
| | 12 Hours | 36 Hours | 60 Hours |
| PLURONIC ® F 127 | 8.0 | 8.0 | 3.0 |
| Glycerol | 1.0 | 1.75 | 1.0 |
| Triacetin | 2.0 | 1.0 | 1.0 |

Discussion

The vehicles demonstrating minimal direct bacteriostatic activity are used to formulate lysostaphin and serially dilute it below its minimum inhibitory concentration (MIC). The inhibitory profile as measured by the reduction of the optical density at 650 nM in the presence of the vehicle is then compared to that of lysostaphin diluted in Mueller-Hinton Broth. In Table III, results are shown for poloxamer 407 NF and triacetin. Both vehicles potentiate the MIC (bacteriostatic effect) of lysostaphin, 20–30 fold for poloxamer 407 NF and 4–8 fold for triacetin. Furthermore, as little as 0.12% poloxamer 407 NF potentiates the bacteriostatic effect of lysostaphin by as much as 20 fold.

TABLE III

| POTENTIATION OF BACTERIOSTATIC ACTIVITY OF LYSOSTAPHIN (MIC of Lysostaphin Formulate in Vehicles) | | | | | | | |
|---|---|---|---|---|---|---|---|
| Vehicle | Final Concentration of Formulation | | | | | | |
| PLURONIC ® F127 | 15% | 3% | 0.6% | 0.12% | 0.024% | 0.0048% | CONTROL[1] |
| | $0.0037^2$ | $0.0037^2$ | $0.0075^2$ | $0.03^2$ | $0.03^2$ | $0.03^2$ | 0.125 |
| Triacetin | 10% | 1.0% | 0.1% | 0.01% | 0.001% | 0.0001% | CONTROL[1] |
| | $<0.000007^3$ | $<0.000007^3$ | $0.06^3$ | 2.0 | 0.5 | 1.0 | 1.0 |

[1]Control MIC is the MIC of lysostain in saline and diluted in MHB.
[2]Concentrations of vehicles in significant potentiation of lysostaphin MIC activity is observed.
[3]Bacteriostatic activity is accounted for by vehicle alone (i.e., direct bactericidal activity).

EXAMPLE 3

Potentiation of Lysostaphin Bacteriostatic Activity (Minimum Inhibitory Concentration).

Dissolved in 15% w/v poloxamer 407 NF is 512 μg/mL of lysostaphin by adding 487.4 μl of a 2.5 mg/mL aqueous solution to 1512.6 μl of the 15% w/v poloxamer 407 NF in sPBS. The lysostaphin is first filtered through a 0.22 μ filter and the concentration is adjusted (1.19 factor). The poloxamer 407 NF is mixed overnight and filtered through a 0.22μ cellulose acetate filter. In a similar fashion, preparations with other vehicles such as lysostaphin in triacetin are prepared.

Lysostaphin in Mueller-Hinton Broth is run as a control and a 512 μg/mL solution is prepared from the same 2.5 mg/mL solution as the poloxamer 407 NF mixture. Placed in 189 μl of Mueller-Hinton Broth is 61 μl of the 2.5 mg/mL solution.

Placed in the first well of a 12 well row is 100 μl of each mixture and serial two-fold dilutions are performed in Mueller-Hinton Broth through row 12. Following dilution, 50 μl of inoculum is added to each well. Inoculum is prepared by inoculating a tube of trypticase soy broth (TSB) from an overnight trypticase soy agar (TSA) culture containing a 10% sheep blood plate of *Staphylococcus aureus* (Newbould 305). The tube is incubated for 5 hours at 37° C. with constant agitation. Following incubation, 20 μl of the five hour culture is added to 100 mL of Mueller-Hinton Broth. Plate counts are performed on the inoculum.

Prepared in 15% poloxamer 407 NF is 128 μg/mL of lysostaphin as follows, starting with a 2.5 mg/mL stock solution:

$$V_1 = \frac{1000 \ \mu l \times 128 \ \mu g/mL}{2500 \ \mu g/mL} = 51.2 \ \mu l \times 1.19 \ (\text{factor}) =$$

60.9 μl into 939.1 μl of 15% Poloxamer 407 NF

EXAMPLE 4

Potentiation of Lystostaphin Bactericidal Activity

Preparation of 50% glycerol and 15% poloxamer 407 NF plus lysostaphin is as follows: The lysostaphin stock of 2.5 mg/mL is thawed and filtered through a 0.22μ filter.

$$V_1 = \frac{1000 \ \mu l \times 1000 \ \mu g/mL}{2500 \ \mu g/mL} =$$

400 μl × 1.19 (correction factor) =

476 μl of 2.5 mg/mL into 524 μl of 50% Glycerol or

15% Poloxamer 407 NF $$V_1 = \frac{4 \ mL \times 64 \ \mu g/mL}{1,000 \ \mu g/mL} =$$

256 μl into 3744 μl of 50% Glycerol or 15%Poloxamer 407 NF

In a similar fashion, triacetin solutions are also prepared.

Mueller-Hinton Broth containing lysostaphin is prepared as above. Penicillin in Mueller-Hinton Broth is prepared to serve as a control. Starting with a frozen 2.5 mg/mL stock solution the penicillin is diluted as follows: 400 μl of 2.5 mg/mL is placed in 600 μl of Mueller-Hinton Broth to yield a 1000 μg/mL solution. Added to 3744 μl of Mueller-Hinton Broth is 256 μl of the 1000 μg/mL solution to yield a 64 μg/mL solution.

Placed in sterile tubes are 2 mL of the vehicle and lysostaphin; Mueller-Hinton Broth plus lysostaphin; and Mueller-Hinton Broth plus penicillin. Serial two-fold dilutions are performed by hand using 1 mL of the appropriate vehicle as the diluent. Lysostaphin and penicillin dilutions range from 64 μg/mL to 0.25 μg/mL. All combinations are done in duplicate. The *Staphylococcus aureus* is grown for 5 hours in 5 mL of TSB and 0.1 mL is removed and placed in 9.9 mL of saline. Each tube is inoculated with 100 μl of the diluted culture. Plate counts are performed on the inoculum. All tubes are incubated for 18 hours at 37° C. with constant agitation. Following incubation, each dilution of lysostaphin in the vehicles or Mueller-Hinton Broth and penicillin in Mueller-Hinton Broth is diluted in phosphate buffered saline to $10^{-2}$, $10^{-4}$ and $10^{-6}$.

Plated on a TSA with 10% sheep blood is 100 μl of the undilute and of each dilution. The plates are inverted and incubated for 18 hours. Following incubation, the number of colonies on each plate is counted.

Discussion

The vehicles which inhibit the growth or are moderately bactericidal to S. aureus by themselves are unable to be evaluated using the MIC procedure. For these vehicles a minimum bactericidal concentration assay (MBC) is performed. This assay in conjunction with the previous MIC data distinguish bacteriostatic effects versus bactericidal effects of the vehicles. Various formulations are mixed with lysostaphin at a final concentration of 32 μg/mL. Ten, serial two- or four-fold dilutions of the lysostaphin are performed in the vehicle and each tube inoculated with a 2-6 x's 106 S. aureus CFU's (bacterial colony-forming units). Samples are removed after 18 hours and plated on blood agar plates. The data in Table IV summarize these results.

TABLE IV

POTENTIATION OF BACTERICIDAL ACTIVITY OF LYSOSTAPHIN BY VEHICLES
Survival of S. aureus CFU (Log 10) in Vehicles

| Vehicle | Concentration of Lysostaphin (μg/mL) | | | | | | |
|---|---|---|---|---|---|---|---|
| | 8 | 4 | 2 | 1 | 0.5 | 0.25 | 0 |
| Lysostaphin (MHB) | $3.3^3$ | $4.8^3$ | $3.6^3$ | $8.1^2$ | 8.6 | 9.7 | 9.3 |
| 10% Triacetin + lysostaphin | 0 | 5.13 | $-^1$ | $5.2^3$ | — | $6.3^2$ | 7.7 |
| 15% PLURONIC ® F127 + lysostaphin | $2.0^3$ | $4.9^3$ | $7.3^2$ | 7.9 | 8.1 | — | 8.5 |
| 50% Glycerol + lysostaphin | 0 | $2.3^3$ | $2.5^3$ | $2.5^3$ | — | — | 9.1 |
| Penicillin | 0 | $3.1^3$ | — | $2.5^3$ | $4.2^3$ | — | 9.4 |

[1](—) indicates S. aureus survival not determined at this concentration.
[2]Greater than 95% killing of S. aureus.
[3]Greater than 99.99% killing of S. aureus.

EXAMPLE 5

Efficacy of Lysostaphin Formulated in Vehicles as an Intramammary Infusion Preparation Against *Staphylococcus Aureus* Mastitis This experiment examines the ability of various lysostaphin formulations to eliminate S. aureus infections in the bovine mammary gland and compares the formulations with the testing of lysostaphin in a peanut oil-gel matrix, similar to that used in the commercial product CEFA-LAK ®, which is used to treat mastitis in lactating dairy cows.

Lysostaphin is formulated in three vehicles: 15% w/v poloxamer 407 NF, 50% w/v glycerol or 10% w/v triacetin. Lysostaphin is also formulated in a peanut oil-gel matrix. These formulations are infused into the bovine mammary gland and the ability of these combinations to exact a biological response, either by curing the infection or by clearing the mammary gland temporarily of S. aureus, are assessed.

Recombinant lysostaphin is suspended in 10.0 mL of peanut oil vehicle or dissolved in 60.0 mL of appropriate sterile vehicle (sPBS) at a concentration of 10.0 mg/mL or 1.67 mg/mL, respectively. Each of 15% poloxamer 407 NF (PLURONIC ® ACID F127, a polyoxyethylene-polyoxypropylene derivative, BASF Corporation, Parsippany, N.J.); 50% glycerol (Sigma Chemical Co., St. Louis, Mo.); and 10% triacetin (glyceryl triacetate, Sigma Chemical Co., St. Louis, Mo.) are prepared in sterile phosphate buffered saline.

*Staphylococcus aureus* infections of the mammary gland provide an excellent model system for evaluating therapeutic efficacy of a variety of pharmaceutical and biological agents for many infectious diseases of mammals. Therefore, experimental infections are established with S. aureus (strain Newbould 305). All mammary glands to be inoculated are free of pathogens and have individual quarter somatic cell counts (SCC) less than 200,000 cells/mL of milk. Inoculum is prepared from a four-hour culture grown in trypticase soy broth and diluted. Inoculations are made by infusion of 1.0 mL diluted culture containing 90 colony forming units of S. aureus (Newbould 305) into the teat cistern of a milked-out mammary quarter. Quarters which fail to establish an infection after six days from initial inoculation are reinfected.

Prepared in PBS is 50% glycerol and the solution is then sterile filtered (0.45μ). Poloxamer 407 NF is mixed overnight and prepared similarly. A 10% triacetin solution is prepared aseptically in sterile PBS. Appropriate amounts of lysostaphin is added so the final concentration is 1.67 mg/mL. All preparations are in a total volume of 60.0 mL and made the day of the infusion. All solutions are sterile filtered through a 0.45μ filter.

Experimental Procedure A

No. of cows: 8
No. of quarters available for treatment: 32
Duration of treatment: 3 consecutive PM milkings

| Treatment Groups: | Number of Quarters: |
|---|---|
| 50% glycerol | 3 |
| 10% triacetin | 3 |
| 15% PLURONIC ® F127 | 3 |
| 50% glycerol + 100 mg lysostaphin | 8 |
| 10% triacetin + 100 mg lysostaphin | 8 |
| 15% PLURONIC ® F127 + 100 mg lysostaphin | 7 |

Quarters are randomly assigned to one of six treatment groups. All quarters are infused with the appropriate vehicle (60.0 mL) with or without lysostaphin over three consecutive PM milkings.

Experimental Procedure B

No of cows: 6
No. of quarters available for treatment: 24
Duration of treatment: 3 AM or PM milkings
Treatment Groups:
   100 mg lysostaphin in 10.0 mL peanut oil (LO); frequency 3x; # of qtrs=6
   100 mg lysostaphin in 10.0 mL sPBS (L); frequency 3x; # of qtrs=6

All quarters are randomly assigned to one of four treatment groups. Quarters receive the assigned treatment over designated milkings. Lysostaphin in peanut oil (10.0 mL) is infused over three consecutive PM milkings.

Discussion

In vitro findings demonstrate that the activity of lysostaphin (bacteriostatic and/or bactericidal) against S. aureus are potentiated by formulating lysostaphin in certain vehicles. To demonstrate the in vivo potency, the infected quarters are infused with lysostaphin (100 mg) formulated in the various vehicles. The results are summarized in Table V.

TABLE V

SUMMARY OF EFFICACY OF LYSOSTAPHIN FORMULATED IN VARIOUS VEHICLES

| Treatment[1] | # Quarters | % Cures (#) | Mean Clearing +/− S.D. |
|---|---|---|---|
| Lysostaphin[2] (saline) | 31 | 19.4 (6) | 7.3 +/− 4.4 |
| Lysostaphin (15% PLURONIC ® F127) | 7 | 57.1 (4) | 9.6 +/− 6.6 |
| Lysostaphin (50% Glycerol) | 8 | 25.0 (2) | 6.8 +/− 4.6 |
| Lysostaphin (10% triacetin ®) | 8 | 25.0 (2) | 6.0 +/− 5.1 |
| Lysostaphin[3] (peanut oil) | 4 | 0.0 (0) | 4.0 +/− 4.0 |

[1]All animals received 100 mg infusions of lysostaphin on three consecutive days in the indicated formulations.
[2]Lysostaphin in saline is pooled data from three different trials.
[3]Lysostaphin formulated in peanut oil is data obtained from infected multiparous cows in differing stages of lactation.

Lysostaphin formulated in poloxamer 407 NF elicits the best cure rate with 57% cures, and an average of 9.6 clear milkings of relapsed quarters. This represents a 2–3 fold improvement of the therapeutic efficacy of lysostaphin formulated in saline. Neither glycerol nor triacetin (both have a cure rate of 25%) has any significant effect on potentiating the in vivo efficacy of lysostaphin. Lysostaphin in a similar formulation to CEFA-LAK ® (peanut oil base) cures 0% of the treated quarters.

EXAMPLE 6

Evaluation of Recombinant Bovine Interleukin-2 Formulated in Poloxamer 407 NF as a Therapeutic for S. aureus Mastitis This experiment compares r-BoIL-2 formulated in poloxamer 407 NF, against CEFA-LAK ® (cephapirin in a commercial formulation), Na cephapirin (in PBS) and r-BoIL-2 in combination with Na cephapirin (in PBS) as potential therapeutics for S. aureus mastitis. The study employs the following materials: recombinant bovine interleukin-2 (r-BOIL-2, Immunex Corporation, Seattle, Wash.); CEFA-LAK ® (200 mg cephapirin as cephapirin sodium in a commercially packaged dose, Bristol-Meyers, Evansville, Ind.); 200 mg Na cephapirin dissolved in 10.0 mL sterile saline; PLURONIC ® ACID F127 (poloxamer 407 NF, BASF Corporation, Parsippany, N.J.).

The treatment of Holstein-Fresian dairy cattle is run over three days. There are four treatment groups as follows:

Treatment 1=2 infusions consisting of 200 mg cephapirin (as CEFA-LAK ®), at 0 and 12 hours.

Treatment 2=3 infusions consisting of 10 mg r-BoIL-2/poloxamer 407 NF at 0, 24 and 48 hours.

Treatment 3=3 infusions consisting of 3.3 mg r-BoIL-2 in 10 mL PBS at 0, 24 and 48 hours, followed by 2 infusions of 200 mg Na cephapirin in 10 mL PBS at 0 and 12 hours.

Treatment 4=2 infusions consisting of 200 mg Na cephapirin in 10 mL PBS at 0 and 12 hours.

All mammary glands to be infused have been infected with S. aureus (Newbould 305). Infusions are made into the teat cistern of a milked out mammary gland after the prescribed milking. In quarters that are to be infused with both a cytokine and a cephapirin (treatment 3), the cytokine will be infused first followed by the cephapirin. All quarters have been randomly assigned to one of four treatment groups according to length of infection and location of quarter (i.e., front or rear). All quarters have been positive for S. aureus infection for at least 14 days. The results are summarized in Table VI.

TABLE VI

COMPARISON OF FORMULATIONS

| Group | Treatment | Dose | Response (%)[1] | Cure (%)[2] |
|---|---|---|---|---|
| 1 | CEFA-LAK ® | 200 mg | 100 | 53.8 |
| 2 | r-BoIL-2 + PLURONIC ® F127 | 10 mg | 38 | 38.5 |
| 3 | r-BoIL-2 + cephapirin | 3.3 mg/200 mg | 85 | 61.5 |
| 4 | Cephapirin | 200 mg | 85 | 23.1 |

[1]% RESPONSE - The number of quarters which culture negative for S. aureus at the first sampling following the last treatment, divided by the total number of quarters per treatment group.
[2]% CURE - A quarter is considered to fail if ≧ 1 S. aureus colony is cultured for 3 consecutive days or ≧ 20 S. aureus colonies are cultured for 2 consecutive days, over a seven day period between days eight and fifteen following the final treatment. Number of failures are then subtracted from the total number of quarters per group and this number is used to determine percent cure (# cure/total # per group × 100% = % CURE).

EXAMPLE 7

Evaluation of Recombinant Bovine Interleukin-2 and Recombinant Bovine Interleukin-1 Formulated 407 NF as a Therapeutic for S. aureus Mastitis An experiment is conducted to determine the efficacy of recombinant bovine interleukin-2 or recombinant bovine interleukin-1, in a poloxamer 407 NF formulation (PLURONIC ® ACID F127) against an established S. aureus infection. A total of 46 infected glands are randomly assigned to one of four treatment groups according to length of infection and location (front vs. rear). Milk samples are plated daily for bacteriology prior to the start of treatment, the day following the last treatment and from day eight through day fifteen following the last treatment. Plates are scored as either positive or negative for S. aureus colonies and scores are used to determine the percent response and percent cure for each treatment group. Rate of response is within ranges previously observed from similar doses using a PBS carrier. While overall cure rates are poor, the poloxamer 407 NF formulation of the cytokines is equivalent to the CEFA-LAK ® cure rate. The poor cure rates may be a result of chronic infections or pockets of walled off S. aureus within the gland. The results are reported in Table VII.

TABLE VII

COMPARISON OF FORMULATIONS

| Group | Treatment | Dose | Response (%)[1] | Cure (%)[2] |
|---|---|---|---|---|
| 1 | CEFA-LAK ® | 200 mg | 90 | 20 |
| 2 | IL-2 + Na Cephapirin + PLURONIC ® F127 | 3.3 mg/200 mg | 82 | 18 |
| 3 | IL-1 + Na Cephapirin + | 200 µg/200 mg | 100 | 27 |

TABLE VII-continued

COMPARISON OF FORMULATIONS

| Group | Treatment | Dose | Response (%)[1] | Cure (%)[2] |
|---|---|---|---|---|
| | PLURONIC ® F127 | | | |

[1] % RESPONSE - The number of quarters which culture negative for *S. aureus* at the first sampling following the last treatment, divided by the total number of quarters per treatment group.

[2] % CURE - A quarter is considered to fail if ≧ 1 *S. aureus* colony is cultured for 3 consecutive days or ≧ 20 *S. aureus* colonies are cultured for 2 consecutive days, over a seven day period between days eight and fifteen following the final treatment. Number of failures are then subtracted from the total number of quarters per group and this number is used to determine percent cure (# cure/total # per group × 100% = % CURE).

EXAMPLE 8

Evaluation of Toxicosis and Milk Production Following Infusions of r-Boil-1 and r-BoIL-2 Combinations Daily observations of dairy cattle are made for any signs of toxicosis following the beginning of treatment. When compared to previous experiments using a phosphate buffered saline (PBS) carrier, there is no significant difference in observable signs of toxicosis (for example, rectal temperature, udder edema, appetite, etc.) with either cytokine. A decrease of adverse clinical signs are observed when cytokines (for example, r-BoIL-2) are formulated in PLURONIC ® ACID F127 as compared to equivalent doses administered in PBS. Results are shown in Table VIII.

TABLE VIII

TOXICOSIS FOLLOWING r-BoIL-2 AND r-BoIL-1 FORMULATED INFUSIONS

| Group | Treatment | Total Dose[1] | Edema[2] | Rectal Temp.[3] |
|---|---|---|---|---|
| 1 | CEFA-LAK ® | 400 mg | 0% | normal |
| 2 | IL-2 + Na Cephapirin PLURONIC ® F127 | 9.9 mg/ 400 mg | 9% | normal |
| 3 | IL-2 + Na Cephapirin in sPBS | 9.9 mg/ 400 mg | 23% | normal |
| 4 | IL-1 + Na Cephapirin PLURONIC ® F127 | 400 μg/ 400 mg | 36% | normal |
| 3 | IL-1 + Na Cephapirin in sPBS | 400 μg/ 400 mg | 23% | normal |
| 4 | Na Cephapirin PLURONIC ® F127 | 400 mg | 0% | normal |

[1] TOTAL DOSE = total dose received per quarter over the entire treatment period.
[2] EDEMA = number of glands expressing tenderness and/or swelling divided by the total number of glands per group × 100%.
[3] RECTAL TEMP. = rectal temperatures are recorded daily for five days following the initiation of treatment. No elevation is observed for any of the treatment groups.

Milk weights as a subtle measure of toxic effects are also recorded daily throughout the treatment period and compared to the five days prior to treatment. Cows receiving a total dose of 400 μg r-BoIL-1/poloxamer 407 NF exhibit around a 30% decrease in milk production on day two of treatment with production levels returning to normal by day four. This is a significant observation when compared to a 60% production decrease at equivalent dose levels using a PBS carrier. Animals receiving a total dose of 9.9 mg r-BoIL-2/poloxamer 407 NF exhibit an equivalent decrease in production when compared to data from experiments using similar dose rates with a PBS carrier. The data of the milk production are shown in Table IX.

TABLE IX

MILK PRODUCTION FOLLOWING r-BoIL-2 AND r-BoIL-1 FORMULATED INFUSIONS

| Treatment (Dose) | Decrease (%) for Number of Days Post-infusion | | | | | | |
|---|---|---|---|---|---|---|---|
| | 1 | 2 | 3 | 4 | 5 | 6 | 7 |
| r-BoIL-1/sPBS (200 μg) | 60.7 | 54.5 | 22.3 | 3.1 | 3.9 | 2.3 | 2.9 |
| r-BoIL-1/ PLURONIC ® (200 μg) | 31.7 | 29.5 | 8.5 | 0 | 1.0 | 0 | 2.0 |
| r-BoIL-2/sPBS (10.0 mg) | 28.3 | 64.6 | 65.9 | 54.4 | 35.7 | 23.9 | 16.2 |
| r-BoIL-2/ PLURONIC ® (10.0 mg) | 7.3 | 1.7 | 6.4 | 7.3 | 0 | 0 | 0 |

EXAMPLE 9

Selection of Vehicles for Lysostaphin Formulations by Toxicity

Several surfactants, detergents, oils, emollients and membrane solubilizers are chosen as representative of various classes of compounds which may affect protein activity. These vehicles are then evaluated for toxicity and potentiation of the bacteriostatic effects of r-lysostaphin on *S. aureus* according to the methods described in the foregoing examples. First, the toxicity of the vehicles to *S. aureus* is determined by using the minimum inhibitory concentration (i.e., the concentration of the vehicle which shows 80–90% growth inhibition). Secondly, the vehicles are subjected to the toxicity test on murine cells in vitro. Viable cells are evaluated by trypan blue exclusion and normalized to an untreated control. Thereafter, dairy cattle are infused through the teat canal with various concentrations of the vehicle to make a determination of the irritation potential after intramammary infusion as a measure of mammalian toxicity. Milk samples are collected after infusion of said vehicles and the somatic cell count is determined. The Stimulation Index equals the post-infusion SCC divided by the pre-infusion SCC. The vehicles showing minimal toxicity to *S. aureus* and mammalian cells in vitro and in vivo are subsequent candidates for evaluation in the in vivo potentiation trials.

EXAMPLE 10

Evaluation of Potentiation of Bacteriostatic Activity of Lysostaphin by Vehicles Various vehicle combinations are tested in a standard checkered analysis which simultaneously varies the concentration of both parameters to examine the individual contribution of each. Vehicles are all compared to r-lysostaphin in a saline solution, i.e., the potentiation index. As can be seen in the below Table X, the PLURONICS ® and GENEROLS ® as vehicles demonstrate the best potentiation of the bacteriostatic effect of r-lysostaphin over a wide concentration range. Glycerol and triacetin, while only potentiating the activity of r-lysostaphin 6–8 fold, is manifested by bactericidal effects (see above Table IV).

TABLE X

POTENTIATION OF BACTERIOSTATIC ACTIVITY OF LYSOSTAPHIN BY VEHICLES

| | Vehicle Conc. w/Max. Potentiation (%) | Potentiation Index Compared to Lysostaphin[1] |
|---|---|---|
| Glycerol | 50.0 | 6–8[2] |
| Triacetin | 10.0 | 6–8[2] |
| PLURONIC ® F127[3] | 0.006 | 436.0 |
| PLURONIC ® F88 | 0.0004 | 28.0 |
| PLURONIC ® 25 R8 | 0.0036 | 54.8 |
| PLURONIC ® F68 | 0.0018 | 113.0 |
| PLURONIC ® F88 in propylene glycol | 0.0004 | 28.0 |
| PLURONIC ® P84 | 0.0004 | 435.0 |
| PLUROFLO ® E-4B4 | 2.5 | 103.2 |
| PLURONIC ® F87 | 0.625 | 258.0 |
| Propylene Glycol | 0.195 | 0.9 |
| GENEROL ® 122 E 25[5] | 0.0009 | 113.0 |
| GENEROL ® 122 E 10 | 0.25 | 258.0 |
| GENEROL ® 122 E 16 | 2.5 | 103.2 |
| n-Dodecylglucosid | 0.078 | 1025.0[6] |
| Decanoyl-n-methylglucamid | 0.078 | 258.0 |
| Dodecyl B-D-maltosid | 0.0024 | 64.5 |
| Octanoyl-n-methylglucamid | 0.31 | 25.6 |

TABLE X-continued

POTENTIATION OF BACTERIOSTATIC ACTIVITY OF LYSOSTAPHIN BY VEHICLES

| | Vehicle Conc. w/Max. Potentiation (%) | Potentiation Index Compared to Lysostaphin[1] |
|---|---|---|
| n-Octylglucosid | 0.039 | 1.0 |
| Dodecylpoly(ethylene glycol)ether | 0.0012 | 1.0 |

[1]Potentiation Index is calculated by dividing the M.I.C. of r-lysostaphin in a saline solution by the M.I.C. of r-lystostaphin in formulation with the vehicle.
[2]Potentiates the bactericidal activity of r-lysostaphin.
[3]PLURONIC ® is a registered trademark of BASF Corp., Parsippany, NJ, for a series of polyoxypropylene-polyoxyethylene block copolymers.
[4]PLUROFLO ® is a registered trademark of BASF Corp., Parsippany, NJ, for a mixture of a polyoxypropylene-polyoxyethylene block copolymer, N-butanol and water.
[5]GENEROL is a registered trademark of Henkel Corp., Hoboken, NJ, for 10–25 moles ethylene oxide soya sterol.
[6]Shows significant potentiation at this single concentration. Potentiation is eliminated when diluted four-fold.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

We claim:

1. A therapeutic composition which comprises a potentiating or safening amount of an aqueous surfactant in combination with a tumor necrosis factor, wherein the surfactant is a sterol, n-dodecylglucosid, decanoyl-n-methylglucamid, dodecyl B-D-maltosid or octanoyl-n-methylglucamid.

* * * * *